United States Patent
Bonnette et al.

(10) Patent No.: US 9,050,127 B2
(45) Date of Patent: Jun. 9, 2015

(54) CONSOLIDATED ATHERECTOMY AND THROMBECTOMY CATHETER

(71) Applicant: Boston Scientific Limited, Hamilton (BM)

(72) Inventors: Michael J. Bonnette, Minneapolis, MN (US); Debra M. Kozak, Forest Lake, MN (US); Eric J. Thor, Arden Hills, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 192 days.

(21) Appl. No.: 13/794,350

(22) Filed: Mar. 11, 2013

(65) Prior Publication Data

US 2014/0005699 A1    Jan. 2, 2014

Related U.S. Application Data

(60) Provisional application No. 61/664,975, filed on Jun. 27, 2012.

(51) Int. Cl.
*A61B 17/22*     (2006.01)
*A61B 17/3207*   (2006.01)

(52) U.S. Cl.
CPC . *A61B 17/320758* (2013.01); *A61B 17/320725* (2013.01); *A61B 2017/22079* (2013.01); *A61B 2217/005* (2013.01); *A61B 2217/007* (2013.01)

(58) Field of Classification Search
CPC ............ A61B 17/32002; A61B 2017/320024; A61B 17/320758; A61B 17/320725; A61B 17/3207; A61B 17/320783; A61B 2017/320775

USPC ........................................................ 606/159
See application file for complete search history.

(56) References Cited

U.S. PATENT DOCUMENTS 5,261,877 A * 11/1993 Fine et al. ..................... 604/540
5,273,526 A * 12/1993 Dance et al. .................... 604/35
(Continued)

FOREIGN PATENT DOCUMENTS

WO    2008042987    4/2008

OTHER PUBLICATIONS

International Search Report and Written Opinion mailed Oct. 16, 2013 from the counterpart PCT Application No. PCT/US2013/046751 filed on Jun. 20, 2013.

*Primary Examiner* — Jonathan W Miles
(74) *Attorney, Agent, or Firm* — Seager, Tufte & Wickhem LLC

(57) ABSTRACT

An atherectomy and thrombectomy system includes a catheter body extending between proximal and distal catheter portions. The catheter body includes an aspiration lumen extending therein. An atherectomy assembly is coupled with the distal catheter portion and includes a rotatable cutter. A thrombectomy assembly is coupled with the distal catheter portion. The thrombectomy assembly includes a jet body within the aspiration lumen, and inflow and outflow orifices extending through the catheter body and in communication with the aspiration lumen. In a thrombectomy configuration a cyclical flow is generated by the jet body through the outflow and inflow orifices to hydrodynamically abrade thrombus, the cyclical flow entrains thrombus and delivers thrombus into the aspiration lumen. In the atherectomy configuration the rotatable cutter cuts plaque into plaque particulate, and the cyclical flow of the thrombectomy assembly entrains the particulate and delivers the particulate into the aspiration lumen.

16 Claims, 10 Drawing Sheets

(56) References Cited

U.S. PATENT DOCUMENTS

| | | | |
|---|---|---|---|
| 5,496,267 A | 3/1996 | Drasler et al. | |
| 6,224,570 B1 | 5/2001 | Le et al. | |
| 6,565,588 B1 | 5/2003 | Clement et al. | |
| 6,818,001 B2 | 11/2004 | Wulfman et al. | |
| 6,926,726 B2 | 8/2005 | Drasler et al. | |
| 6,936,056 B2 * | 8/2005 | Nash et al. | 606/159 |
| 7,344,546 B2 | 3/2008 | Wulfman et al. | |
| 7,842,009 B2 | 11/2010 | Torrance et al. | |
| 7,935,077 B2 | 5/2011 | Thor et al. | |
| 2002/0138088 A1 * | 9/2002 | Nash et al. | 606/159 |
| 2002/0198550 A1 * | 12/2002 | Nash et al. | 606/159 |
| 2003/0114869 A1 * | 6/2003 | Nash et al. | 606/159 |
| 2003/0216760 A1 | 11/2003 | Welch et al. | |
| 2004/0006358 A1 * | 1/2004 | Wulfman et al. | 606/167 |
| 2004/0181249 A1 * | 9/2004 | Torrance et al. | 606/170 |
| 2004/0220519 A1 | 11/2004 | Wulfman et al. | |
| 2008/0103516 A1 * | 5/2008 | Wulfman et al. | 606/170 |
| 2008/0275393 A1 | 11/2008 | Bonnette et al. | |
| 2009/0326568 A1 * | 12/2009 | Shturman | 606/159 |
| 2010/0324472 A1 * | 12/2010 | Wulfman | 604/22 |
| 2011/0152908 A1 | 6/2011 | Morris et al. | |
| 2012/0239065 A1 * | 9/2012 | Bonnette et al. | 606/159 |

\* cited by examiner

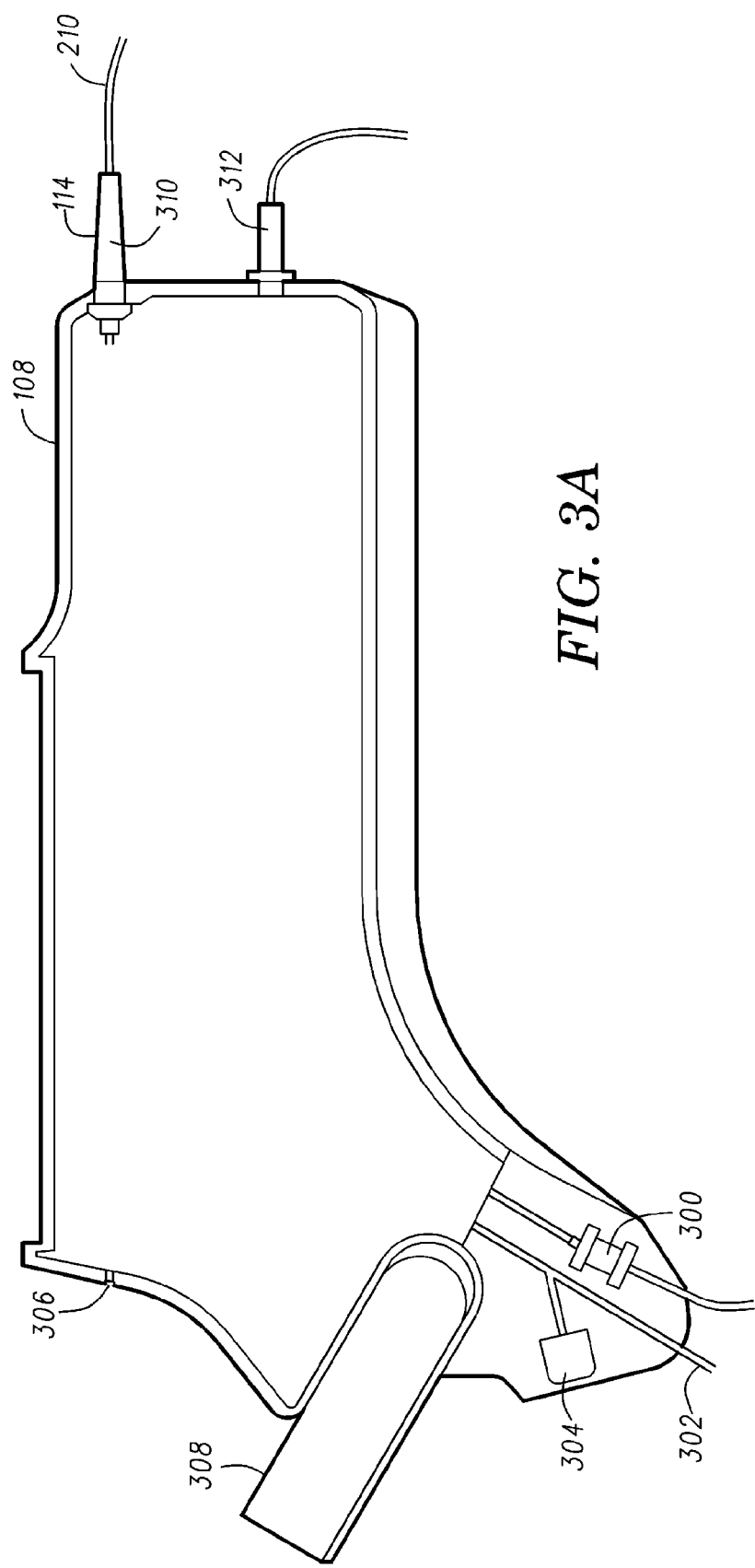

CONSOLIDATED ATHERECTOMY AND THROMBECTOMY CATHETER

CLAIM OF PRIORITY

This patent application claims the benefit of priority, under 35 U.S.C. Section 119(e), to Bonnette et al., U.S. Provisional Patent Application Ser. No. 61/664,975, entitled "CONSOLIDATED ATHERECTOMY AND THROMBECTOMY CATHETER," filed on Jun. 26, 2012, which is hereby incorporated by reference herein in its entirety.

TECHNICAL FIELD

This document pertains generally, but not by way of limitation, to atherectomy and thrombectomy.

BACKGROUND

Atherectomy and thrombectomy are procedures for removing plaques and thrombus from the vasculature. Plaques are more robust and anchored to the vessel walls relative to thrombus, which has a softer consistency and is more easily removed from the vessel.

In some examples, atherectomy catheters remove plaques from vessel walls through mechanical engagement and abrasion of plaques. The mechanical removal of plaques generates loose particulate matter within the vessel wall that increases the risk of emboli within the blood stream.

Similarly, in some examples, thrombectomy procedures remove thrombus from vessel walls through mechanical systems that mechanically engage and remove thrombus, for instance by cutting of the thrombus with one or more features at the end of a catheter. In still other examples, catheters include hydrodynamic features that generate streams of solution, such as saline, that engage with thrombus and hydrodynamically remove thrombus from the vessel walls. In yet other examples, solutions such as lytic medicants are delivered to thrombus within the vasculature, and the medicants breakdown the thrombus.

Overview

The present inventors have recognized, among other things, that a problem to be solved can include the identification and discrimination of various features of the vasculature, for instance plaques and thrombus. It is difficult with a single device to identify plaques (that may require more robust treatments) from thrombus. Each accrues along the vessel walls, and may accrue in the same location. In an example, the present subject matter can provide a solution to this problem, such as by combining a thrombectomy function that cooperates with an atherectomy function in a single catheter. For instance, by including one or more inflow orifice subject to a cross stream flow, the inflow orifice aspirates loose thrombus at a region of interest within the vessel. Plaque along the vessel is left behind and readily identified through imaging.

In combination with a thrombectomy assembly including an inflow and outflow orifice, an atherectomy catheter provides thrombectomy capabilities at the vessel site, for instance through introduction of a cyclical flow of infusion solution through the inflow and outflow orifices by way of an interior jet loop (e.g., a jet body). The thrombectomy assembly macerates and aspirates thrombus from the vessel thereby revealing any plaque at the location for removal by the atherectomy assembly of the catheter. The catheter system (including both the thrombectomy and the catheter) is thereby able to easily, and without the exchange of catheters, mechanically abrade the plaque. Optionally, the jet loop along with outflow orifices are used to introduce contrast fluid to the vessel site to further assist in imaging of plaque and accordingly provide a better target for the atherectomy assembly.

Additionally, the thrombectomy assembly, including for instance one or more inflow openings, cooperates with the atherectomy assembly to rapidly remove loose particulate matter generated by the mechanical abrasion of the atherectomy procedure. For instance, the jet loop inside the catheter body delivers one or more cross stream jets across one or more inflow openings and through a venturi effect macerates the particulate matter (e.g., embolized plaque) and draws it into the aspiration lumen of the catheter substantially before the particulate matter can move downstream from the atherectomy assembly. Similarly, the thrombectomy assembly operates during thrombectomy procedures (using cyclical flow as described herein) to macerate loose thrombus and draw the thrombus into the aspiration lumen for delivery to an effluent receptacle. Optionally, the thrombectomy assembly operates during either or both of atherectomy or thrombectomy procedures to entrain particulate in the cyclical flow between the inflow and outflow orifices to macerate the particulate matter (whether plaque or thrombus) and delivery the particulate matter eventually along the aspiration lumen to an effluent receptacle.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A is a side view of a manifold housing coupled with a proximal catheter portion of the atherectomy and thrombectomy assembly.

DETAILED DESCRIPTION

Figure 1:
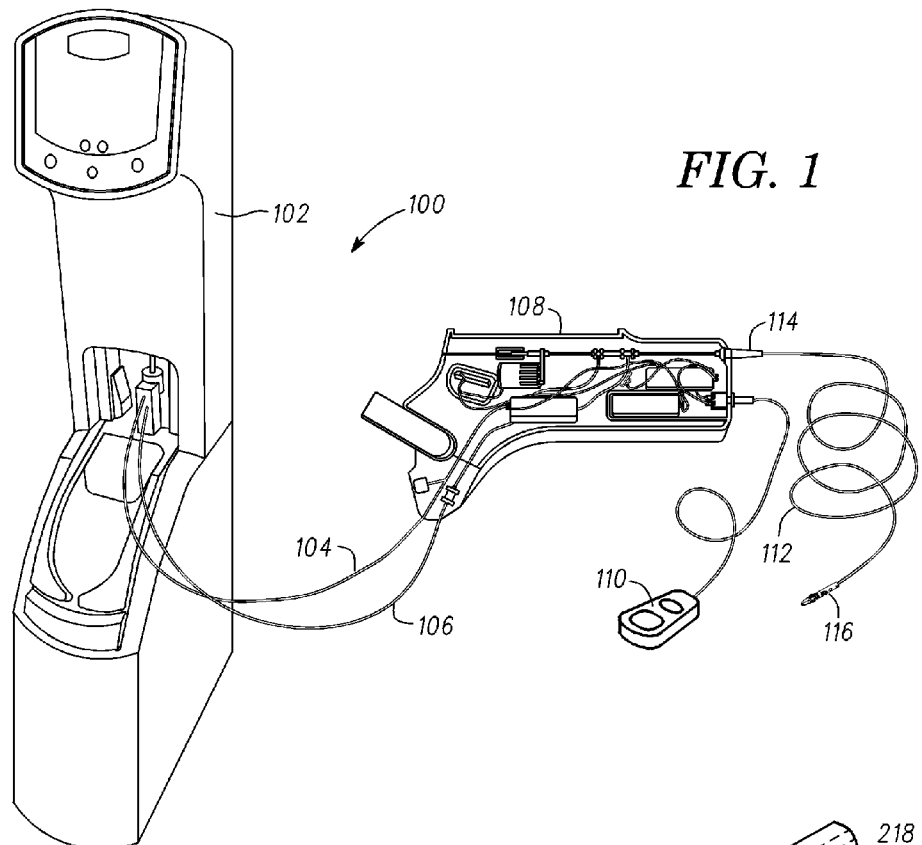
FIG. 1 is an isometric view of one example of a consolidated atherectomy and thrombectomy assembly.

FIG. 1 shows one example of a composite system, for instance, an atherectomy and thrombectomy system 100 configured to perform both of an atherectomy and thrombectomy procedures at a single location within a vessel. Referring to FIG. 1, the composite system 100 includes an infusion and aspiration source 102. For instance, the infusion and aspiration source 102 includes a metering pump configured to provide a source of infusion fluid, for instance, along an infusion line 104 for the catheter 112 shown in FIG. 1. Additionally, the infusion and aspiration source 102 provides an aspiration line 106 coupled with the catheter 112, for instance, through the manifold housing 108 that allows for the aspiration of particulate such as particulate entrained in a returning infusion flow to an aspiration destination, such as an effluent bag and the like. In one example, a negative pressure is applied through the aspiration line 106 by a negative pressure source at the composite system infusion and aspiration source 102 (e.g., a metering pump, vacuum pump, vacuum syringe and the like).

Referring again to FIG. 1, as shown the manifold housing 108 is coupled with the infusion and aspiration source 102 of the composite system 100 with infusion and aspiration lines 104, 106. The infusion and aspiration lines 104, 106 cooperate to provide a source of infusion fluid for the manifold housing 108 and the catheter 112 coupled with the manifold housing as well as aspiration of the infusion fluid including, for instance, bodily fluids and infusion fluids such as saline and entrained particulate such as thrombus and plaque particulate matter therein.

The manifold housing 108 is shown in FIG. 1 with an atherectomy control 110 extending from a portion of the manifold housing 108. In another example, the atherectomy control 110 is incorporated into the manifold housing 108. As will be described in further detail herein, the manifold housing 108 includes a motor and a portion of a drive shaft extending through the catheter 112. The motor and drive shaft are configured to operate the atherectomy assembly at the distal catheter portion 116 of the catheter 112. A proximal catheter portion 114 of the catheter 112 is coupled with the manifold housing 108. The proximal catheter portion 114 allows for a fluid tight seal for the delivery of the infusion fluid from the infusion and aspiration source 102 along the length of the catheter 112, for instance, to the distal catheter portion 116. The atherectomy control 110 operates the drive shaft and motor within the manifold housing 108 and thereby operates the atherectomy assembly at the distal catheter portion 116. The infusion and aspiration source 102 cooperates with a thrombectomy system at the end of the distal catheter portion 116 to dislodge particulate (e.g., thrombus) and remove particulate such as a thrombus and plaque.

As will be described herein, the thrombectomy system and atherectomy systems are able to cooperate and operate together according to their position on the catheter 112. For instance, the atherectomy system dislodges and macerates particulate, such as thrombus and plaque, and the thrombectomy system removes particulate matter such as plaque particulate generated by the atherectomy assembly.

Figure 2:
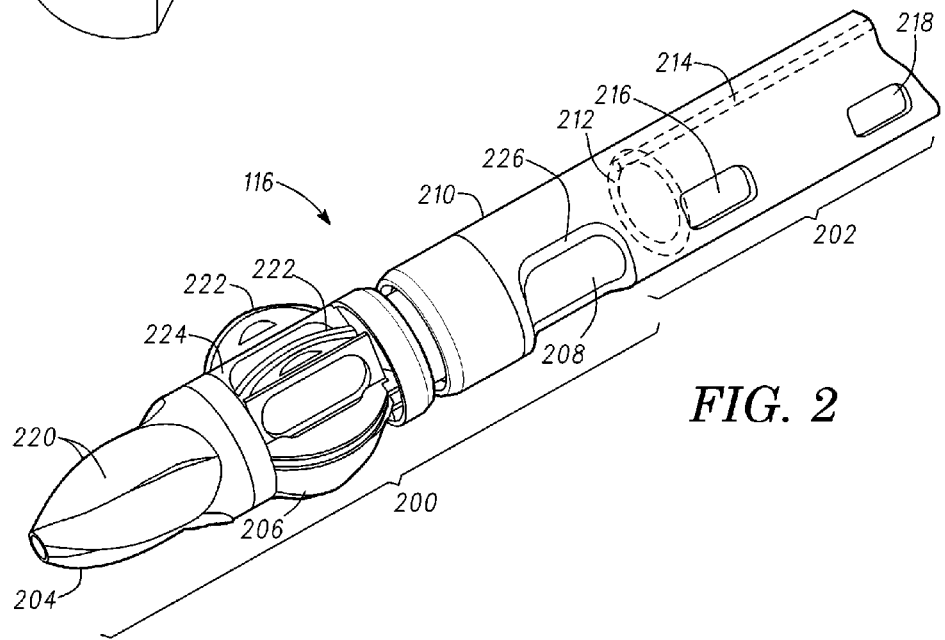
FIG. 2 is a perspective view of a distal catheter portion of the atherectomy and thrombectomy assembly.

FIG. 2 shows the distal catheter portion 116 previously shown in FIG. 1. As shown the distal catheter portion 116 includes an atherectomy assembly 200 including one or more rotatable cutters and the thrombectomy assembly 202 positioned adjacent to the atherectomy assembly 200. In another example, the thrombectomy assembly 202 is spaced relative to the atherectomy assembly 200. For instance, in one example, the thrombectomy assembly 202 is positioned distally relative to the atherectomy assembly 200. In still another example, the thrombectomy assembly 202 is spaced from the atherectomy assembly 200, for instance, by positioning of the thrombectomy assembly 202 further down the catheter body 210, for instance, toward the proximal catheter portion 114 previously shown in FIG. 1.

As shown in FIG. 2, in one example the atherectomy assembly 200 includes one or more rotatable cutters. In one example, the atherectomy assembly 200 includes a distal tip cutter 204 including one or more blades rotatable relative to the catheter body 210, for instance, through operation of a drive shaft described in detail below. In another example, the atherectomy assembly 200 includes an expandable cutter 206 having one or more expandable cutting members 222 as shown in FIG. 2. As will be described in further detail below, in one example, the expandable cutting members 222 are rotatably coupled with a spindle 224. The spindle 224 is, in one example, rotatably coupled relative to the catheter body 210. Additionally, the spindle 224 is fixedly coupled with the drive shaft and rotation of the drive shaft correspondingly spins the spindle. With rotation of the spindle in a particular direction the expandable cutting members 222 are deployed relative to the spindle into the configuration shown in FIG. 2 to facilitate the cutting of plaque from a vessel wall.

In another option, the atherectomy assembly 200 includes a macerator 208 positioned proximal relative to the distal tip cutter 204 and the expandable cutter 206. Optionally, the macerator 208 is included as one of the rotatable cutters of the atherectomy assembly 200. As shown in FIG. 2, the macerator 208 is positioned within a portion of the catheter body 210 and is exposed to the exterior of the catheter body 210, for instance, through a macerator port 226.

As will be described in detail herein, the plurality of rotatable cutters including, for instance, one or more of the distal tip cutter 204, the expandable cutter 206 and the macerator 208 are configured to mechanically engage with material within a vessel, such as a plaque, and cut the material from the vessel wall thereby freeing the plaque and forming a particulate within the vessel. In one example, the macerator 208 is configured to macerate the particulate material and draw the material into the catheter body 210 for eventual delivery along an aspiration lumen, for instance, to the infusion and aspiration source 102 shown in FIG. 1 (e.g., an effluent bag).

In another example, the macerator 208 is not included in the atherectomy assembly 200. Instead, the thrombectomy assembly 202 (described herein) is provided with the distal tip cutter 204 and the expandable cutter 206 of the atherectomy assembly 200. In one example, the thrombectomy assembly 202 is positioned distally relative to the position shown in FIG. 2 and accordingly closer to the rotatable cutter 206. As will be described herein the thrombectomy assembly 202 cooperates with the atherectomy assembly 200 (the cutters 204, 206) to assist in the dislodging of particulate (plaques and thrombus). In another example, the thrombectomy assembly 202 cooperates with the cutters 204, 206 to remove particulate in the vessel through the recirculating flow provided by the inflow and outflow orifices 216, 218. Optionally, by moving at the least the inflow orifice 216 into close proximity to the cutters 204, 206 aspiration of particulate may be enhanced.

Referring again to FIG. 2, the thrombectomy assembly 202 is shown in phantom lines within the catheter body 210. In one example, at least a portion of the thrombectomy assembly 202, for instance, the jet body 212 is positioned within an aspiration lumen of the catheter body 210. As shown in FIG. 2, the thrombectomy assembly 202 includes the jet body 212 as well as at least one inflow orifice 216 and at least one outflow orifice 218 spaced from the inflow orifice 216. The jet body 212 is configured to provide one or more jets of infusion fluid, the infusion fluid delivered with the infusion tube 214. The jets of the infusion fluid extend past the inflow orifice 216 and the outflow orifice 218 (they cross the inflow and outflow orifice 216, 218). The flow of the infusion fluid, for instance, from the jets created at the jet body 212 creates a cyclical flow of fluid, for instance, by way of the venturi effect where the infusion fluid delivered toward the outflow orifice 218 is delivered outside of the catheter body 210, for instance, through the outflow orifice 218. A negative pressure created at the inflow orifice 216 by the rapidly moving infusion from the jet body 212 draws the infused fluid and entrained particulate from outside of the catheter body 210 into the inflow orifice 216. The drawn in infusion fluid and particulate is macerated of within the cyclical flow and eventually delivered down an aspiration lumen (e.g., with the catheter 112), for instance, to the infusion and aspiration source 102 shown in FIG. 1.

As will be described in detail herein, the atherectomy assembly 200 and the thrombectomy assembly 202 cooperate to facilitate thrombectomy and atherectomy procedures at the same location within a vessel. For instance, the thrombectomy assembly 202 is able to clarify a region within the vessel containing one or more of plaque and thrombus to successfully remove the thrombus from around a plaque and thereby reveal a plaque for operation of the atherectomy assembly 200. The atherectomy assembly 200 is thereafter operated to cut the plaque from the vessel wall. Cutting of the plaque creates loose particulate plaque within the vessel. The particulate plaque is drawn into the catheter body 210, for instance, by operation of the thrombectomy assembly 202 (or the macerator 208). The particulate matter is, in one example, drawn in through the inflow orifices 216 and thereafter macerated by cyclical flow of the particulate matter through the inflow orifice and outflow orifices 216, 218. The jet body 212 thereafter delivers the particulate matter along the catheter body 210, for instance, through an aspiration lumen within the catheter 112 to the infusion and aspiration source 102 shown in FIG. 1.

Figure 3B:
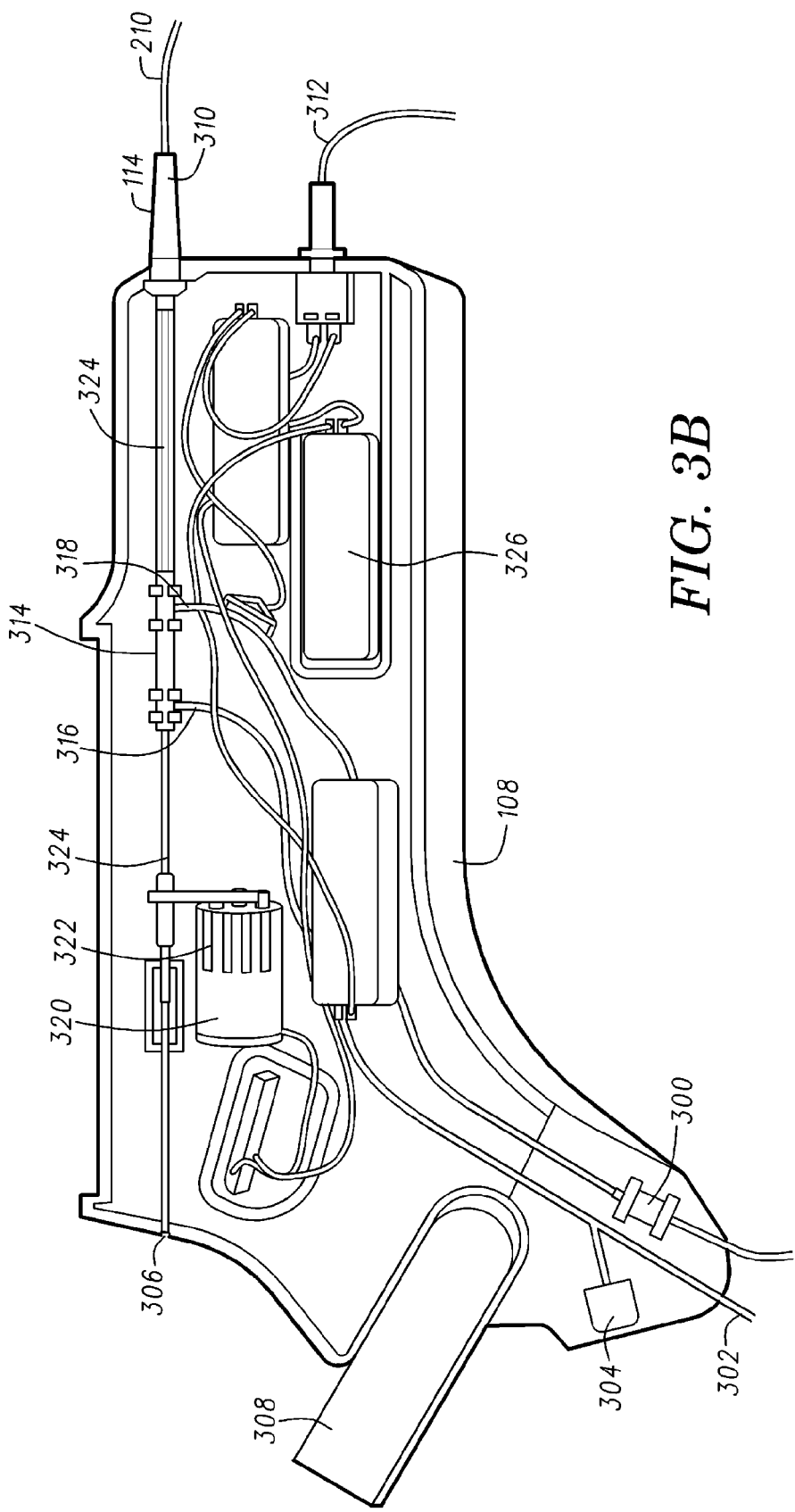
FIG. 3B is a cross section view of the manifold housing of FIG. 3A.

FIGS. 3A and 3B show exterior and cross-sectional views of the manifold housing 108 previously shown in FIG. 1, respectively. Referring first to FIG. 3A, the manifold housing 108 includes an aspiration port 300 and an infusion port 302. The aspiration port 300 is configured for coupling with the aspiration line 106 running between the infusion and aspiration source 102 and the manifold housing 108. Similarly, the infusion port 302 couples with the infusion line 104 running between the infusion and aspiration source 102 and the manifold housing 108. The aspiration and infusion ports 300, 302 thereby provide for aspiration and infusion of fluid to the catheter body 210, for instance, at a catheter fitting 310 coupled with a proximal catheter portion 114. In another example, an access port 304 is coupled with the infusion port 302. The access port 304 allows for the introduction of fluids such as lytics, medications and the like through the access port 304 and into the infusion line coupled with the catheter body 210.

In another example, the manifold housing 108 includes a guide wire access port 306. In one example, the guide wire access port 306 is aligned with the catheter body 210 extending into the manifold housing 108. The guide wire is delivered through the guide wire access port 306 and into a portion of the catheter 112, for instance, the interior of the drive shaft extending to the distal catheter portion 116 and having the atherectomy assembly 200 positioned therein. As shown in FIG. 3A, the manifold housing 108 includes in another example a guide wire clamp 308. The guide wire clamp 308 is configured to clamp around a guide wire extending through the guide wire access port 306 and thereby statically immobilize the guide wire after delivery through the catheter 112. In another example, the guide wire clamp 308 allows for slidable movement of the guide wire, for instance, through the guide wire access port 306 and the guide wire clamp 308. The guide wire clamp 308 immediately grasps and immobilizes the guide wire after movement of the guide wire is ceased.

As shown at an opposed end of the manifold housing 108, the manifold housing includes a catheter fitting 310 and an atherectomy control fitting 312. In one example, the catheter fitting 310 provides a flexible fitting configured for the reception of a portion of the catheter body 210 such as the proximal catheter portion 114 therein. In a similar manner, the atherectomy control fitting 312 includes a flexible fitting sized and shaped for reception of, for instance, a control wire from the atherectomy control 110 shown in FIG. 1. In another example, controls for the atherectomy assembly 200 (and optionally the thrombectomy assembly 202) are provided on the manifold housing 108. Optionally, the controls on the manifold housing 108 for the atherectomy assembly 200 duplicate the control features included with the atherectomy control 110. In another option, the manifold housing 108 controls provide one or more of duplicate control features and supplemental control features for one or more of the atherectomy or thrombectomy assemblies 200, 202.

Referring now to FIG. 3B, the manifold housing 108 is shown in cross-section. The manifold housing 108 includes the aspiration and infusion ports 300, 302 configured for fluid communication with the infusion and aspiration source 102 previously shown in FIG. 1. Additionally, the manifold housing 108 includes the catheter fitting 310 and the atherectomy control fitting 312. As shown in FIG. 3B, a manifold 314 is positioned within the manifold housing 108. In one example, the manifold 314 includes an aspiration interface 316 sized and shaped to couple the aspiration port 300 with the catheter 112. In another example, the manifold housing 108 includes an infusion interface 318. In one example, the infusion interface 318 is positioned distally relative to the aspiration interface 316. Optionally, the infusion interface 318 introduces an infusion tube into the catheter 112, for instance, the proximal catheter portion 114 along an aspiration lumen therein. The manifold 314 thereby facilitates the introduction of an infusion tube into the catheter body 210 as well as a pathway for effluent, for instance, fluid including entrained particulate matter therein to be delivered to the aspiration port 300 and eventually the infusion and aspiration source 102 previously shown in FIG. 1.

Referring again to FIG. 3B, the manifold housing 108 further includes an atherectomy drive motor (e.g., a motor) 320 disposed therein. Optionally, a transmission 322 is provided between the atherectomy drive motor 320 and a drive shaft 324. As shown, the drive shaft 324 extends in a coincident manner with the catheter body 210. As will be described in further detail below the drive shaft 324 extends through the catheter body 210 to the distal catheter portion 116 where the drive shaft 324 is coupled with the atherectomy system 200. Optionally, the manifold housing 108 includes a battery system 326 positioned therein. The battery system 326 is configured to operate the atherectomy drive motor 320. In another example, a separate source of energy such as compressed air, hydraulics, electrical power and the like is provided separate from the manifold housing 108, for instance, through a cable or other connection to thereby operate the drive shaft 324 and the atherectomy drive motor 320 of the manifold housing 108. In one example, the separate source of energy includes cabling (and possibly an in-line power conditioning housing or "box") coupled with the infusion and aspiration source 102. Optionally, the cabling and an in-line box for power conditioning (and in one example control) are reusable and retained with the infusion and aspiration source 102 for later use with other atherectomy assemblies or atherectomy and thrombectomy assemblies as described herein.

Figure 4:
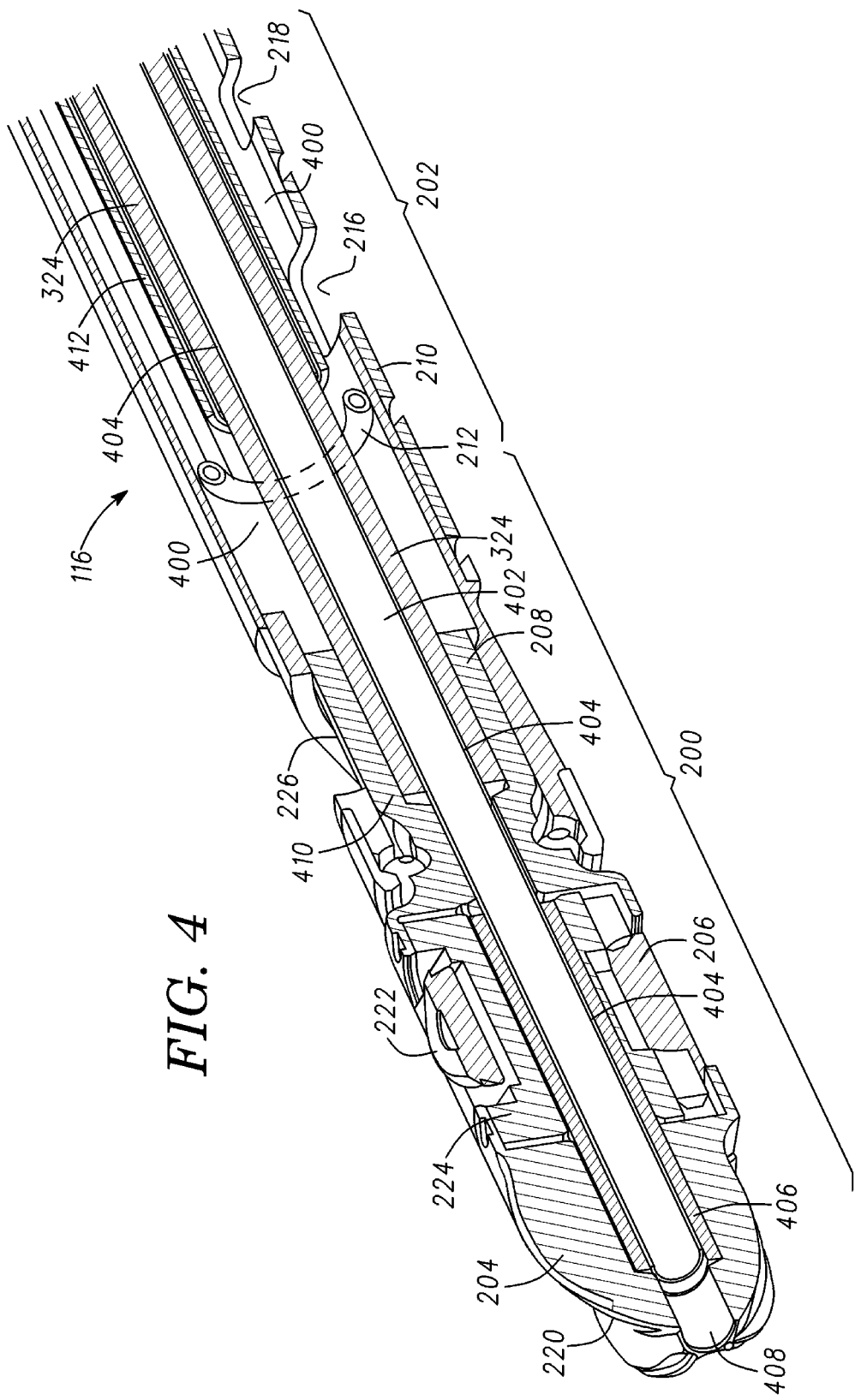
FIG. 4 is a cross sectional view of the distal catheter portion of FIG. 2A including atherectomy and thrombectomy systems.

FIG. 4 shows on example of the distal catheter portion 116 with a composite system 100 (including, for instance, the atherectomy and thrombectomy systems described herein). As shown the distal catheter portion 116 includes the atherectomy assembly 200 including one or more rotatable cutters thereon as well as the thrombectomy assembly 202 configured to cooperate with the atherectomy assembly 200 to thereby enhance the function of both.

In the cross-sectional view shown in FIG. 4, the drive shaft 324 is shown extending from a proximal portion of the distal catheter portion 116 toward a distal portion of the distal catheter portion, for instance, near the distal tip cutter 204. In one example, the drive shaft 324 includes one or more coils, for instance including coil portions wrapped in multiple directions to facilitate the transmission of torsion along the drive shaft 324 without the wrapping of one or more coils that can otherwise cause whipping of the drive shaft 324 in the corresponding catheter body 210. As shown, the drive shaft 324 extends through an aspiration lumen 400 of the catheter body 210. In the distal catheter portion 116 the aspiration lumen 400 extends at least into a portion of the atherectomy assembly, for instance, adjacent to the macerator 208. For instance, the aspiration lumen 400 extends through the thrombectomy assembly 202 and into an adjacent position with the macerator core 410 of the macerator 208.

In one example, the drive shaft 324 extends to the distal catheter portion 116 with a shaft bushing 404 extending along an interior portion of the drive shaft 324. In one example, the shaft bushing 404 is a polymer coating along the interior of the shaft to facilitate the passage of instruments such as guide wires along a guide wire lumen 402 of the drive shaft 324. As further shown in FIG. 4, in one option, a distal bushing 406 is positioned over a portion of the shaft bushing 404 extending distally relative to the drive shaft 324. The drive shaft 324 transmits rotational movement to one or more components of the atherectomy assembly 200 to thereby rotate the macerator 208, distal tip cutter 204 or the expandable cutter 206 relative to the remainder of the catheter body 210. For instance, the drive shaft 324 (including for instance coils formed in series along the catheter body 210) transmits rotational movement to at least the macerator core 410 shown in FIG. 4. The macerator core 410 is fixedly coupled to the spindle 224 of the expandable cutter 206, and rotation of the macerator core 410 thereby correspondingly rotates the spindle 224 to deploy the expandable cutting members 222. In a similar manner, the spindle 224 is coupled with the distal tip cutter 204 and correspondingly rotates the distal tip cutter 204 including the plurality of blades 220 extending therefrom.

In yet another example, the drive shaft 324, for instance, coupled with the macerator core 410 and separately coupled with each of the cutters 204 and 206 transmits rotational movement separately to each of these cutters to thereby separately drive the cutters relative to the catheter body 210. For instance, as shown in FIG. 4, the drive shaft 324 is coupled within the macerator core 410. In another example, the distal bushing 406 is coupled with the shaft bushing 404 which is in turn coupled with the drive shaft 324. The engagement of the distal bushing 406 with one or more of the distal tip cutter 204 and the expandable cutter 206 thereby allows for the separated transmission of rotation to the distal tip cutter 204 and the expandable cutter 206.

In yet another example, the drive shaft 324 is isolated from at least a portion of the aspiration lumen 400 with a shaft sleeve 412. In one example, the shaft sleeve extends around and is spaced from the drive shaft 324 to thereby allow for easy rotation of the drive shaft 324 relative to the remainder of the catheter body 210. For instance, the shaft sleeve 412 is fixedly coupled with a portion of the catheter body 210, such as along a proximal portion of the catheter body proximal relative to the distal catheter portion 116. In another example, the shaft sleeve 412 is fixedly coupled with a portion of the manifold housing 108 shown in FIG. 1. The drive shaft 324 is thereby able to rotate within the shaft sleeve 412 without engagement with components in the thrombectomy assembly 202 including, but not limited to, the infusion tube 214 and the interior wall of the catheter body 210. Instead, the shaft sleeve 412 is lined with or constructed with a low friction material that facilitates transmission of rotation along the drive shaft 324 to the distal catheter portion 116.

Figure 5:
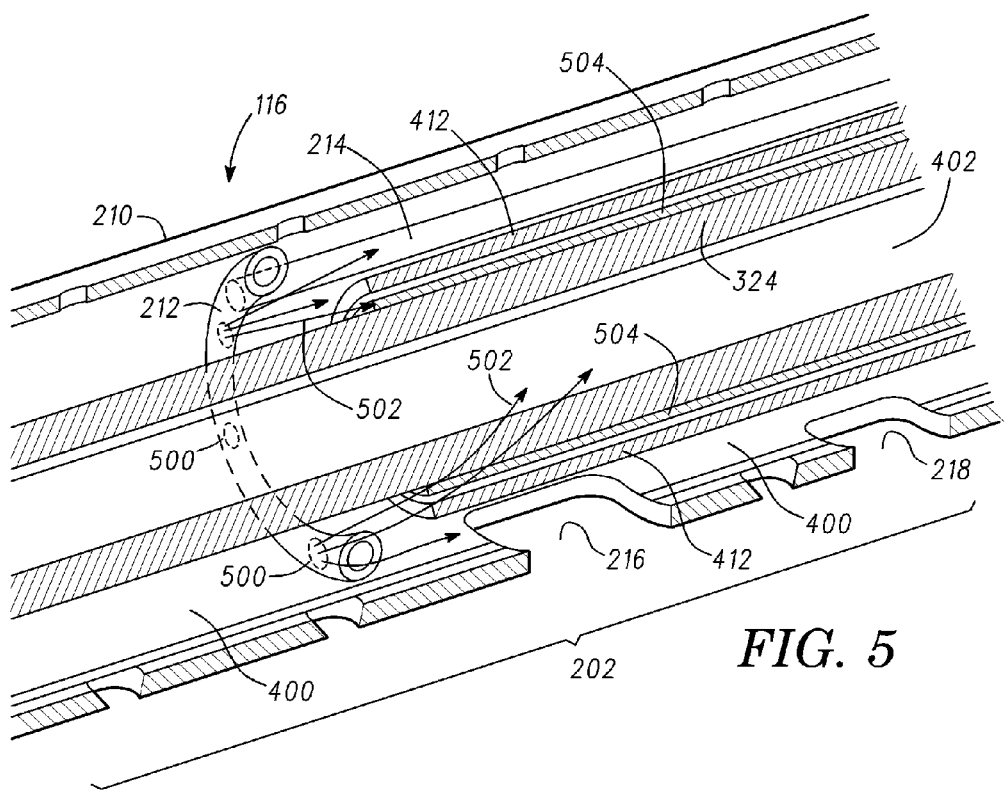
FIG. 5 is a detailed perspective cross sectional view of the thrombectomy system and a portion of the atherectomy system.

Referring now to FIG. 5, a portion of the distal catheter portion 116 including, for instance, the thrombectomy assembly 202 is provided in a detailed cross-section. As previously described, the thrombectomy assembly 202 includes a jet body 212 coupled with an infusion tube 214 extending proximally within the catheter body 210 to the manifold housing 108 previously shown in FIG. 1. The infusion tube 214 is configured to provide a flow of infusion fluid to the jet body 212. The jet body includes a plurality of jet orifices 500 sized and shaped to provide fluid jets 502 directed proximally relative to the catheter body 210. As shown, for instance in FIG. 5, the plurality of fluid jets 502 are directed proximally through the aspiration lumen 400, for instance, to the exterior of the shaft sleeve 412 and into the interior of the shaft sleeve 412 (e.g., between the shaft sleeve 412 and the drive shaft 324). Additionally, in another example the fluid jets 502 are partially directed within the drive shaft 324, for instance, through a plurality of gaps between the coils of the drive shaft and into the guide wire lumen 402.

In one example, the thrombectomy assembly 202 provides a stream of infusion fluid directed proximally according to the positioning of the jet orifices 500 around the jet body 212. As shown in the example of FIG. 5 the plurality of jet orifices 500 are arranged in a proximally directed fashion and thereby correspondingly direct their fluid jets 502 proximally. As further shown in FIG. 5, in one example, the plurality of fluid jets 502 are directed with various portions of the jet flows into different portions of the aspiration lumen 400. One portion of the fluid jets 502 is directed into the region between the shaft sleeve 412 and the inflow and outflow orifices 216, 218. In the region between the shaft sleeve 412 and the inflow and outflow orifices 216, 218 the fluid jets 502 create a cyclical flow into and out of the catheter body 210, for instance, through the orifices 216, 218. The passage of the fluid jets 502 creates a stream of fluid extending out of the outflow orifices 218 that is thereafter drawn into the inflow orifices 216 in a cyclical manner according to a venturi effect as the fluid jets 502 cross the inflow orifice 216. This portion of the flow from the fluid jets 502 accordingly performs a thrombectomy procedure outside of the catheter body 210. The cyclical hydrodynamic flow through the inflow and outflow orifices 216, 218 provides hydrodynamic engagement of the infusion fluid with thrombus, for instance, along a vessel wall and abrades the thrombus from the vessel wall and forces it into inflow orifice 216 where it is thereafter macerated through one or more passes through the inflow and outflow orifices 216, 218 and eventually delivered along the aspiration lumen between the shaft sleeve 412 and the interior of the catheter body 210.

As shown, for instance, in FIG. 5, any thrombus delivered into the inflow orifice 216 is delivered between the shaft sleeve 412 and the catheter body 210. Because of the fluid jets 502 substantially all particulate matters such as thrombus, loose plaque and the like is delivered between the shaft sleeve 412 and the catheter body 210. Because of the distal positioning of the shaft sleeve 412 relative to the inflow orifice 216 in combination with the fluid jets 502 particulate matter is not allowed to move around the shaft sleeve 412 and thereby interpose itself between the shaft sleeve 412 and the drive shaft 324. The drive shaft 324 is accordingly able to freely rotate relative to the shaft sleeve 412 without any substantial ingress of particulate matter such as plaque particles, thrombus particles and the like therebetween.

In another example, another portion of the fluid flow from the fluid jets 502 is directed inwardly, for instance, according to the arrows shown in FIG. 5. In one example, the fluid jets 502 direct a portion of the infusion fluid between the shaft sleeve 412 and the drive shaft 324. For instance, the drive shaft 324 includes a sheath 504 extending along at least a portion of the drive shaft 324. In one example, the sheath 504 includes but is not limited to, a polymer coated along the coils of the drive shaft 324 (e.g., polyimide). In one example, the sheath 504 provides a low friction coating to the drive shaft 324 that facilitates the rotation of the drive shaft 324 relative to the shaft sleeve 412.

Optionally, in a similar manner to the shaft bushing 404, in one example, the sheath 504 is formed along the coils of the drive shaft 324 and is accordingly discontinuous longitudinally along the drive shaft 324 and maintains gaps between the individual coil windings of the drive shaft 324. A portion of the infusion fluid, for instance, shown with the arrows in FIG. 5 is thereby directed through the sheath 504 and the drive shaft 324 and into the guide wire lumen 402. This portion of the infusion fluid directed by the fluid jets 502 thereby lubricates the guide wire lumen 402 and allows for the easy passage and relative rotation of a guide wire within the guide wire lumen 402, for instance, during rotation of the drive shaft 324. Additionally, and as described above, the infusion fluid delivered according to the direction of the fluid jets 502 is delivered between the sheath 504 and the shaft sleeve 412. This flow of infusion fluid provides a lubricant between the rotating drive shaft 324 and the shaft sleeve 412. Any incidental particulate matter or debris lodged between the shaft sleeve 412 and the sheath 504 is lubricated or hydrodynamically pushed down the shaft sleeve 412 to maintain the capability of the drive shaft 324 to rotate relative to the shaft sleeve 412 as well as the remainder of the catheter 210. The thrombectomy assembly 202 is thereby able to provide a lubricating function to the drive shaft 324 of the atherectomy assembly 200 and accordingly maintains the rotatable movement of the drive shaft 324 throughout atherectomy and thrombectomy procedures.

In another example, the shaft sleeve 412 is perforated (includes a series of holes or orifices extending from an outer perimeter to its inner perimeter adjacent to the drive shaft 324. The perforations facilitate the delivery of infusion fluid as a lubricant to the drive shaft in a similar manner. With each of these lubricating arrangements the lubricating infusion fluid in one example fills the gap between the shaft sleeve 412 and the drive shaft 324 to limit the migration of effluent including clogging particulate or fibrin therein. The lubrication of the drive shaft 324 minimizes plugging and seizing of the guidewire within the guidewire lumen 402 and similarly ensures the drive shaft 324 is able to rotate throughout operation of the catheter 112 (e.g., does not seize).

Figure 6:
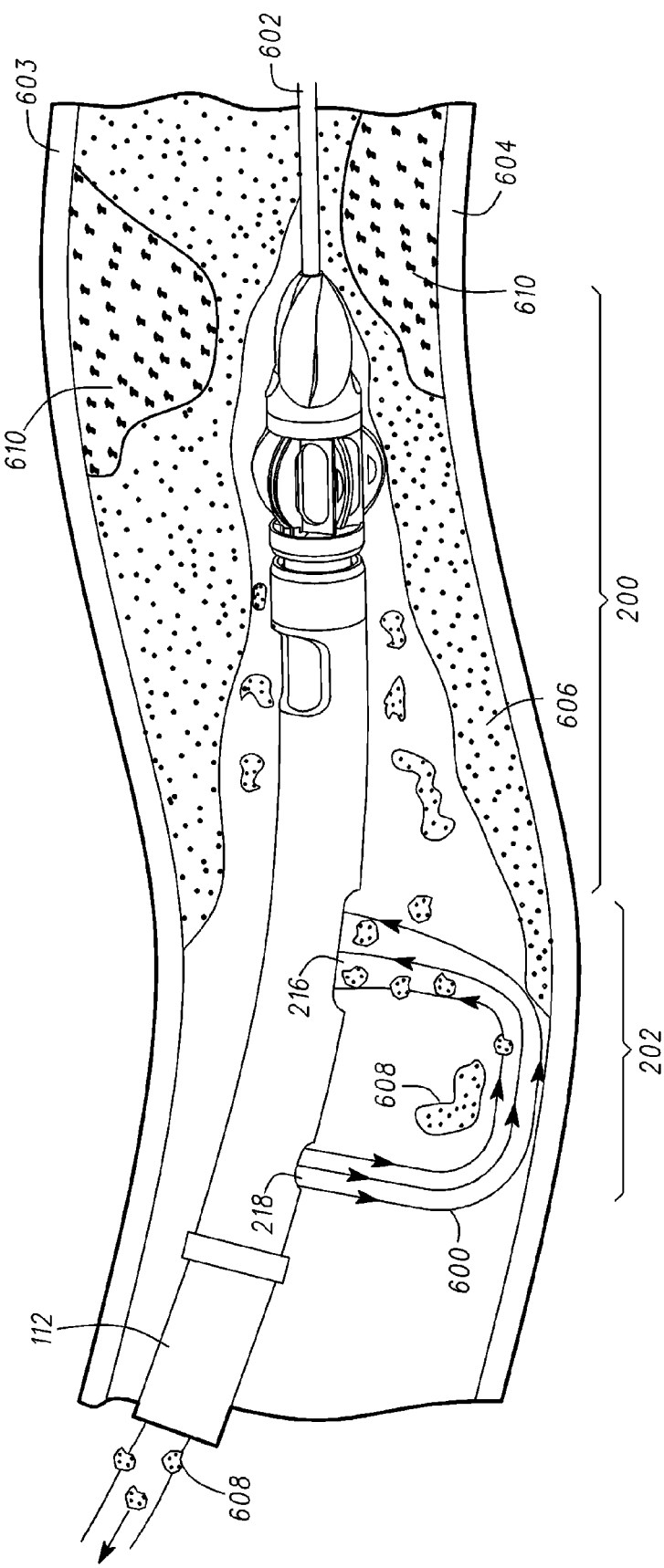
FIG. 6 is a detailed cross sectional view of the thrombectomy system of FIG. 5 in operation within a vessel.

FIG. 6 shows one example of the catheter 112 in operation within a vessel 603 including a vessel wall 604. In the example shown in FIG. 6, the thrombectomy assembly 202 provides a cyclical flow of infusion fluid 600 within the vessel 603. Optionally, the atherectomy assembly 200 is not in an operational mode, for instance, the drive shaft 324 is not operated at this time. In another example, the atherectomy assembly 200 is rotated at the same time as the thrombectomy assembly 202 is operated.

Referring again to FIG. 6, a guide wire 602 is shown extending from the guide wire orifice 408 previously shown in FIG. 4. The guide wire 602 is, in one example, previously delivered through the vessel 603 and allows tracking of the catheter 112, for instance, the distal catheter portion 116 to a location of interest within the vessel 603 such as a location of one or more of thrombus and plaque deposition along the vessel wall 604. As shown in FIG. 6, both thrombus 606 and plaque 610 are positioned along the vessel wall 604.

In operation and as shown in FIG. 6, the thrombectomy assembly 202 is able to clarify the region within the vessel 604 to provide better access and viewing of other features along the vessel wall 604 such as the plaque 612. For instance, with operation of the thrombectomy assembly 202 the cyclical flow 600 of infusion fluid hydrodynamically entrains thrombus particles 608 within the cyclical flow and delivers the thrombus particles 608 through the aspiration lumen 400 previously shown in FIG. 4. This gradual removal of thrombus 606 from the vessel 603 allows for the easy identification of the plaque within the vessel 603. By clarifying the region in the vessel 603 with the suspected plaque 610 therein the physician is able to better visualize the plaque 610, for instance, with imaging methods and thereby operate the atherectomy assembly 200 at a subsequent time to easily remove the plaque 612 at a location of interest without having to unnecessarily remove thrombus 606 where a less aggressive procedure, such as thrombectomy is performed to remove the thrombus 606 from the vessel 603.

In another example, the thrombectomy assembly 202 shown in FIG. 6, is used again after removal of all or substantially all of the thrombus 606 to provide a contrast fluid to the vessel 603. For instance, the delivery of the infusion fluid is substantially interrupted in favor of the delivery of a contrast fluid through the infusion tube 214 and the jet body 212 previously shown in FIG. 2. Delivery of the contrast fluid into the region of the vessel 603 shown in FIG. 6 allows the identification of the plaque 610, for instance, after thrombectomy removal of the thrombus 606. The physician is thereby able to easily identify the plaque 610 and accordingly treat the plaque, for instance, by operation of the atherectomy assembly 200 as described herein.

Figure 7:
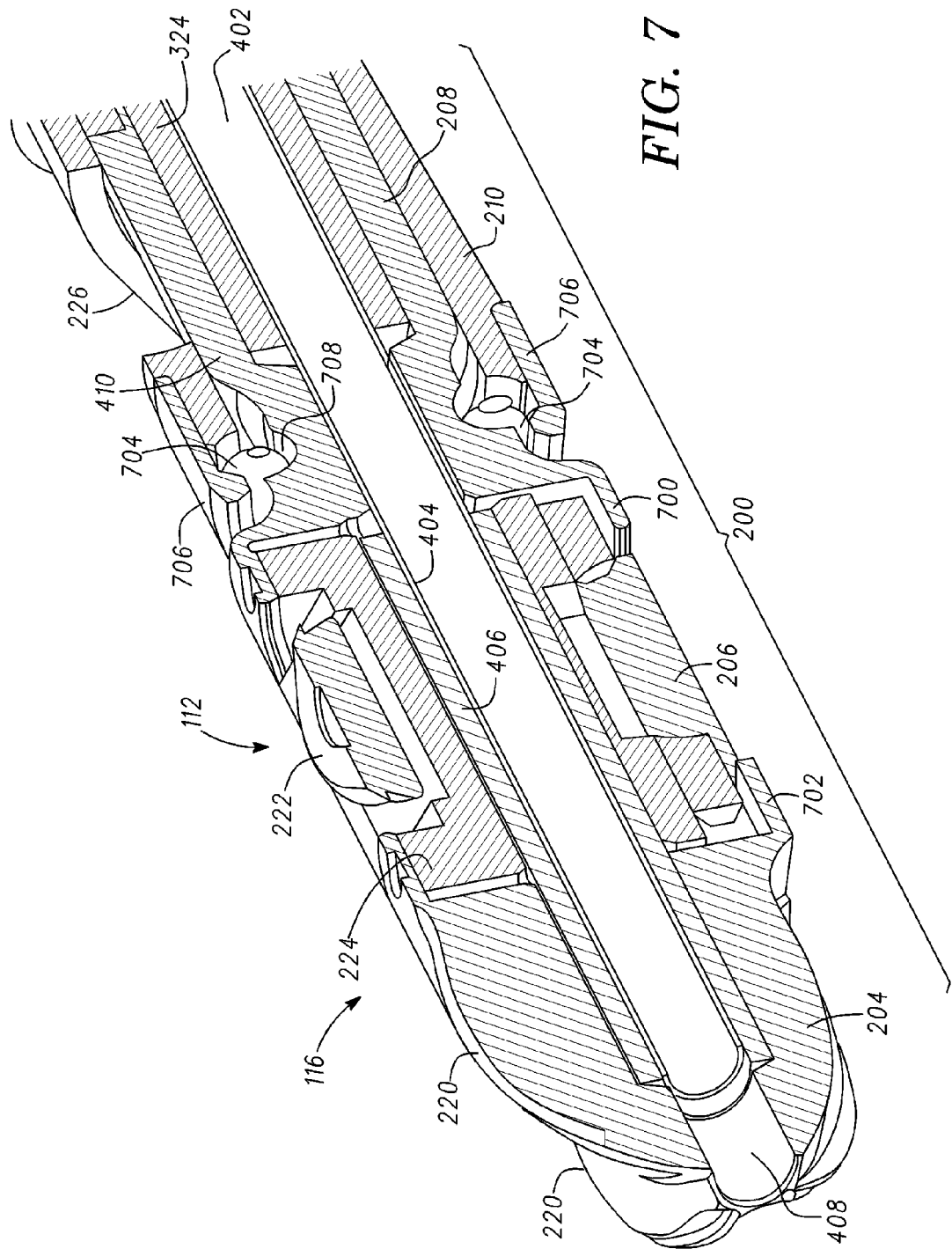
FIG. 7 is a detailed perspective cross sectional view of one example of the atherectomy system.

FIG. 7 shows another portion of the distal catheter portion 116 of the catheter 112 including, for instance, the atherectomy assembly 200. As previously described, in one example, the atherectomy assembly 200 includes one or more cutters configured for performing an atherectomy procedure, for instance, on plaque such as the plaque 610 shown in FIG. 6. In the example shown in FIG. 7, the atherectomy assembly 200 includes a distal cutter 204, an expandable cutter 206 and a macerator 208. As shown, the cutters are formed in series along the distal catheter portion 116. As previously described, the drive shaft 324 is configured to transmit rotation to one or more of the cutters to thereby correspondingly rotate the cutters relative to the remainder of the catheter body 210.

In one example, the drive shaft 324 is coupled with, for instance, the macerator 208 and the macerator 208 is configured to transmit rotation along the distal catheter portion 116, for instance, to the expandable cutter 206 and through rotation of the expandable cutter 206, the distal cutter 204 is also rotated. In another example, the drive shaft 324 includes one or more of a shaft bushing 404 and a distal bushing 406 configured to provide rotational movement to each of the distal cutter 204 and the expandable cutter 206 as previously described herein. In the example wherein the drive shaft 324 transmits rotation to the macerator 208 and the macerator correspondingly transmits rotation distally to each of the expandable cutter 206 and the distal cutter 204 one or more flanges such as a core flange 700 and a cutter flange 702 are provided to fixedly couple the macerator core 410 with the spindle 224 of the expandable cutter 206. The cutter flange 702 is provided to fixedly couple the distal cutter 204 with the spindle 224 of the expandable cutter 206. The flanges 700, 702 thereby cooperate to ensure transmission of rotation distally relative to the macerator 208 as provided by the drive shaft 324.

As further shown in FIG. 7, in one example, the macerator core 410 is rotatably coupled with the catheter body 210. In one example, a plurality of bearings 704 such as ball bearings are interposed between the macerator core 410 and a portion of the catheter body 410, for instance, including a casing 706 extending annularly around the macerator core 410. The plurality of bearings 704 allow for the rotation of the macerator core 410 and at the same time maintain the macerator core 410 at a central position within the catheter body 210. In one example, the casing 706 is a ring such as a metal ring including aluminum, stainless steel, and the like formed around the catheter body 210 with a corresponding groove therein to facilitate the reception of a portion of the bearings 704 therein. A corresponding portion of the macerator core 410 includes a bearing groove 708 therein sized and shaped to receive the bearings 704.

Figure 8:
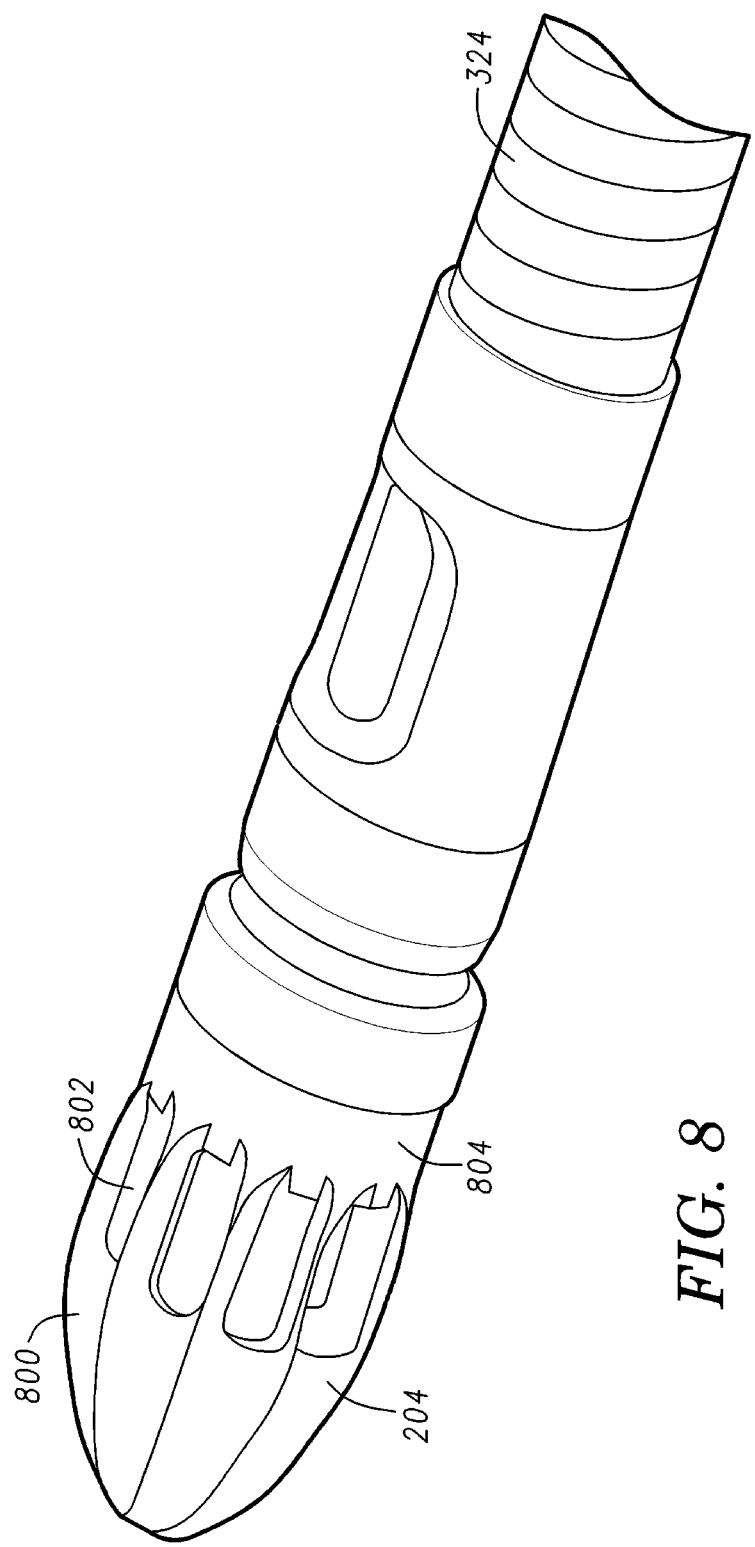
FIG. 8 is perspective view of one example of a rotatable cutter at the distal catheter portion.

FIG. 8 shows another example of distal cutter 204. In the example shown, the cutter 204 includes a plurality of cutting blades 800 including orifices 802 positioned therebetween. In one example, the orifices 802 are in communication with the aspiration lumen 400 previously shown in FIG. 4. In another example, the orifices 802 are in communication with the source of infusion fluid, for instance, provided by the jet body 212. For instance, the jet body 212 includes distally directed orifices sized and shaped to provide a flow of infusion fluid, for instance, to the orifices 802. In one example, the plurality of orifices 802 are sized and shaped for aspiration and the corresponding removal of particulate matter for eventual delivery down the aspiration lumen 400, for instance, by operation of the jet body 212.

As further shown in FIG. 8, in one example, the distal cutter 204 includes a cutter base 804. The plurality of cutting blades 800 extend from the cutter base 804 with the orifices 802 positioned between the blades. In one example, the cutter base 804 is coupled with, for instance, the drive shaft 324 by a flange, such as the cutter flange 702 previously shown in FIG. 7. In another example, the cutter base 804 or any other portion of the distal cutter 204 is coupled with the drive shaft 324, for instance, by an intermediate fitting such as a bushing (e.g., see the bushings 404, 406 shown in FIG. 4).

Figure 9:
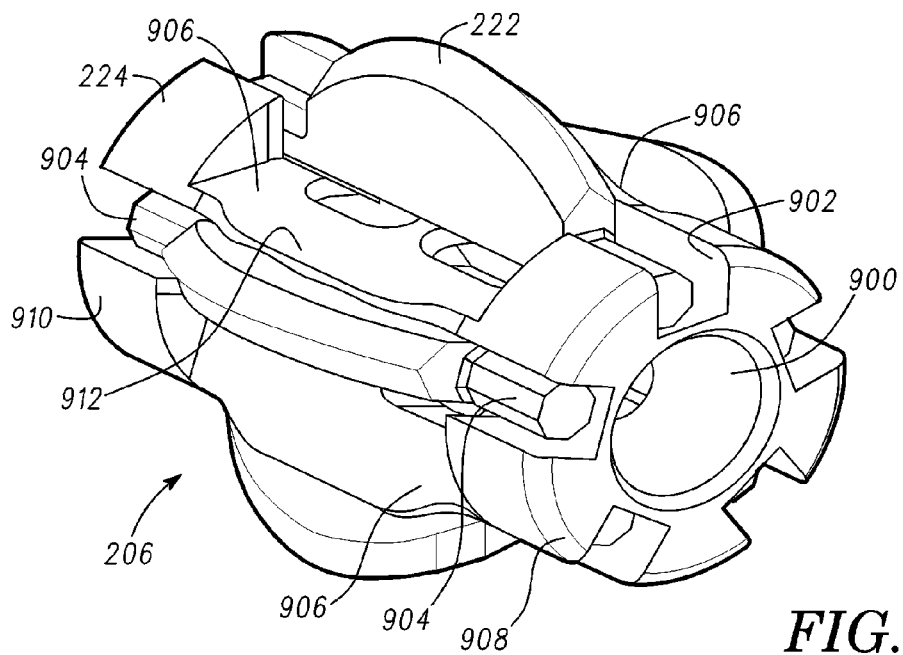
FIG. 9 is an perspective view of one example of a rotatable cutter including a rotating spindle and rotatably mounted cutting members.

Referring now to FIG. 9, one example of a spindle 224 is provided. In the example shown, the plurality of expandable cutting members 222 are shown in an expanded configuration relative to the stored configuration shown in FIG. 7. For instance, in one example, where the spindle 224 is rotated in a counter-clockwise fashion the plurality of expandable cutting members 222 are rotated by centrifugal force into the expanded position shown in FIG. 9. A plurality of support bases 906 engage with the expandable cutting members 222 and thereby support the expandable cutting members 222 in the expanded position. As shown, the expandable cutting members 222 include cutter pins 904 sized and shaped for reception within cutting member recesses 902 formed within the spindle 224. In the example shown in FIG. 9, the plurality of expandable cutting members 222 are arranged in a balanced configuration around the spindle 224. In another example, one or more of the expandable cutting members 222 is removed. This configuration creates an unbalanced expandable cutter 206 and during rotation of the expandable cutter 206 the unbalanced spindle 224 oscillates the catheter laterally, for instance at the expandable cutter 206, relative to the longitudinal axis of the catheter 112. Optionally, this oscillation of the expandable cutter 206 allows for the increased lateral cutting of a plaque 610 within the vessel. Repeated reciprocation of the catheter 112, for instance, to move the expandable cutter 206 into and out of a plaque within the vessel is thereby substantially avoided. Instead, the expandable cutter 206 oscillates laterally and thereby engages with the plaque 610 within the vessel wall without requiring reciprocation or minimizing reciprocation as may otherwise be required with a balanced set of expandable cutting members 222.

In another example, the spindle 224 includes a spindle lumen 900 sized and shaped to receive the drive shaft 324 or a feature associated with the drive shaft such as the bushings 404, 406 therein. As previously described, in one example, the bushings are non-rotatably coupled with the spindle 224 to transmit rotation to the spindle 224 and correspondingly deploy or retract expandable cutting members 222 relative to the spindle 224. For instance, where retraction of the expandable members is desired the spindle 224 shown in FIG. 9 is rotated in a clockwise fashion. Without the support faces 906 to support the expandable cutting member 222 in this direction the expandable cutting members 222 rotate relative to the spindle and thereby are received along the opposed support faces 906 in the contracted configuration. That is to say, the plurality of expandable cutting members 222 are received between the first and second ends 908, 910 of the spindle 224. As shown for instance in FIG. 9, at least a portion of the expandable cutting members 222 are received within corresponding recesses between the first and second ends 908, 910. As shown in FIG. 9 the plurality of storage recesses 912 are sized and shaped to receive a majority of the expandable cutting members 222 therein to form a substantially isodiametric expandable cutter 206 relative to the outer diameter of the catheter body 210 while the cutting members 222 are retracted (e.g., folded along the spindle 224 and within the recesses 912).

Figure 10:
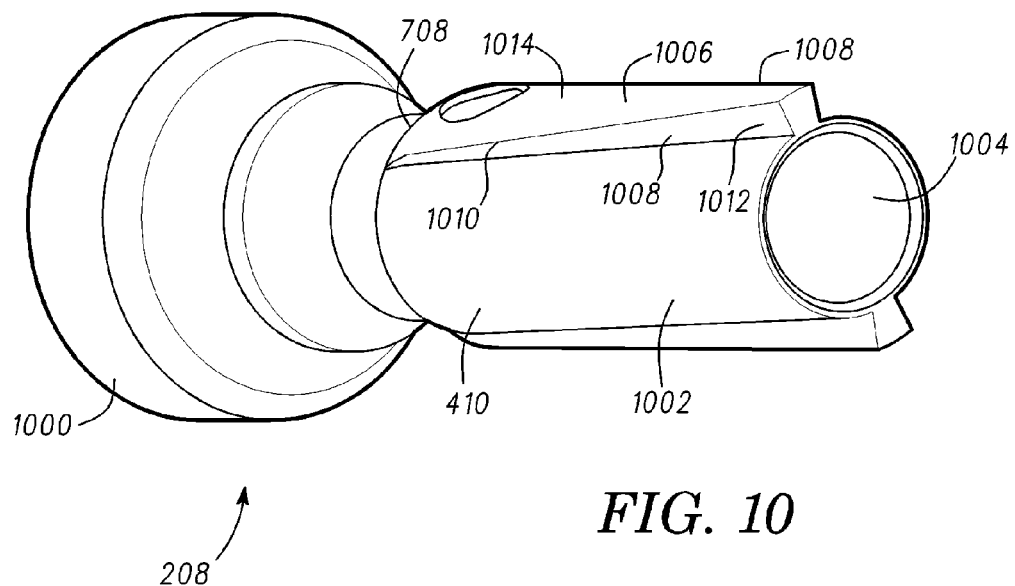
FIG. 10 is an perspective view of one example of a macerator core having projecting bar members.

FIG. 10 shows one example of the macerator core 410 rotatably coupled within the catheter body 210 as previously shown in FIG. 2. This example of the macerator core 410 includes a core base 1000 having a greater diameter than a core barrel 1002. As shown, for instance in FIG. 7, a bearing groove 708 is provided between the core base 1000 and the core barrel 1002 to receive a portion of the ball bearings 704 therein to facilitate rotation of the macerator core 410 within the catheter body 212. The macerator core 410 further includes a core lumen 1004 sized and shaped to receive at least a portion of the drive shaft 324 therein. For instance, in one example, the macerator core 410 is sized and shaped to receive coils of a portion of the drive shaft 324 therein.

Optionally, the coils of the drive shaft are engaged in frictional engagement with the interior of the macerator core 410, for instance, along a wall of the core lumen 1004.

As shown in FIG. 10, the macerator core, for instance, the core barrel 1002 includes one or more projecting bars 1006. The one or more projected bars 1006 include at least one peripheral surface such as a peripheral face 1014 sized and shaped for close and intimate rotation relative to an interior port face, for instance, of the macerator port 226 previously shown in FIG. 2. The close rotation of the projecting bars 1006 along the interior face of the macerator port 226 allows the projecting bars 1006 to cut and macerate particulate matter, for instance, plaque particles, thrombus particles and the like received therein and thereafter deliver those particles into the aspiration lumen 400 (see FIG. 4).

As further shown in FIG. 10, in one example, the plurality of projecting bars 1006 include tapered faces 1008. The tapered faces 1008 are formed along the projecting bars 1006 to facilitate the proximal movement of particulate matter, for instance, infusion fluid including particulate matter therein proximally into the aspiration lumen 400. For instance, during rotation the tapered face 1008 along the core barrel 1002 provides a tapered surface engaged with the infusion fluid including the entrained particulate matter therein. The tapered face, when rotated, thereby drives or moves the entrained fluid along its face and directs the fluid proximally to the aspiration lumen 400. As shown in FIG. 10, in one example, the tapered face 1008 tapers from the first end 1010 toward the second end 1012 positioned proximally relative the core base 1000. For instance, the projected bar 1006 includes opposed tapered faces 1008. In another example, the tapered faces 1008 are tapered relative to a longitudinal axis of the core barrel 1002 (aligned with the longitudinal axis of the catheter 112). In another example, the tapered face 1008 is tapered with regard to its depth between the first and the second end 1010, 1012. For instance, the projected bar 1006 has a greater thickness at the proximal second end 1012 relative to the distal first end 1010. The taper of the projected bar 1006 between the first and second ends 1010, 1012 whether an angular taper as previously described or a depth taper as described now facilitates the delivery of particulate matter, for instance, particulate matter in entrained in fluid proximally along the core barrel 1002 and eventually into the aspiration lumen 400.

Figure 11:
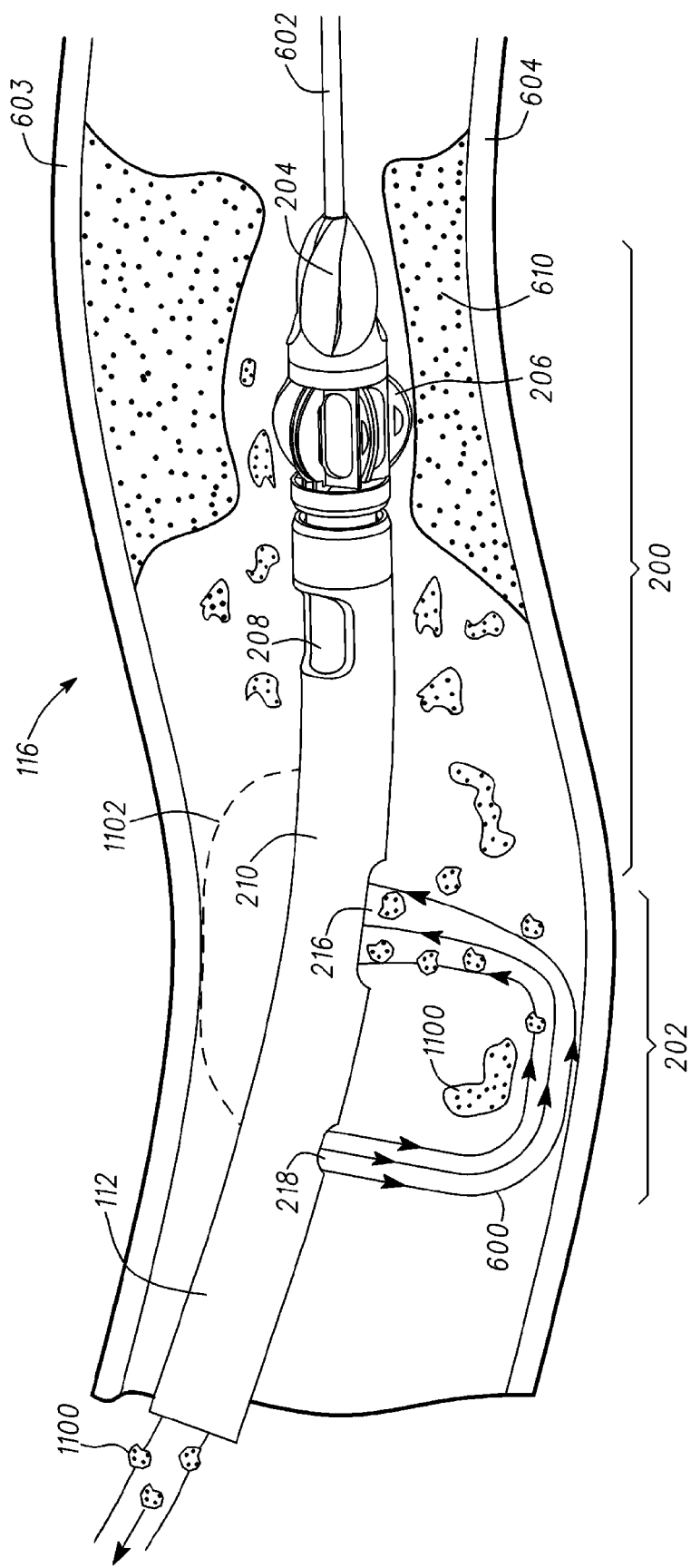
FIG. 11 is a cross sectional view of the catheter of the atherectomy and thrombectomy system in operation within a vessel.

FIG. 11 shows the catheter 112 previously described herein in operation, for instance, during an atherectomy procedure within the vessel 603. As previously shown, for instance in FIG. 6, the catheter 112 is usable in a thrombectomy configuration to clarify a region of the vessel 603 by removing thrombus 606 from the vessel to thereby expose and reveal a plaque 610 within the vessel, for instance, along the vessel wall 604. FIG. 11 shows the plaque 610 originally provided in FIG. 6 in a revealed configuration while the atherectomy assembly 202 is used with the catheter 112 to remove the plaque 610 from the vessel wall 604. As previously described, the atherectomy assembly 202 includes one or more cutters including, for instance, a distal tip cutter 204, expandable cutter 206 and a macerator 208. In the example shown in FIG. 11, the catheter 112 including the atherectomy assembly 202 includes each of the distal tip cutter 204, the expandable cutter 206 and the macerator 208. Each or one or more of these cutters is operated while move through the plaque 610 to cut and remove the plaque 610 from the vessel wall 604. Optionally, one or more of these cutters is absent from the atherectomy assembly 200. For instance, the macerator 208 is removed and instead the drive shaft 324 rotates one or more of the expandable cutter 206 or the distal tip cutter 204.

The removal of the plaque 610 from the vessel wall 604 generates particulate matter 1100 including, for instance, free particles of the plaque 610 entrained, for instance, within the fluid of the vessel. As shown in FIG. 11, the thrombectomy assembly is operated in combination with the atherectomy assembly 202 during this atherectomy procedure. For instance, the cyclical flow 600 of infusion fluid through the inflow and outflow orifices 216, 218 entrains the particulate matter 1100 within the cyclical flow, macerates the particulate matter and delivers it along the aspiration lumen 400 as shown in FIG. 4. Stated another way, the thrombectomy assembly 200 cooperates with the atherectomy assembly 202 to readily remove any free particulate matter 1100 before the particulate matter is able to move down stream relative to the treatment location, for instance, the location of the plaque 616 along the vessel wall 604. Optionally, the thrombectomy assembly 200 includes only one or more inflow orifices. The flow of infusion fluid from the jet body 212 develops a venturi effect at the one or more inflow orifices 216 and draws the particulate matter 1100 into the aspiration lumen 400.

Optionally, the catheter 112 includes one or more of a flow sensor, pressure sensor or the like configured to detect operation of the thrombectomy assembly 202. In another example, the atherectomy assembly 200 is only operated while the thrombectomy assembly 202 is also operated to ensure evacuation of free particulate from the treatment location. For instance, the flow sensor, pressure sensor or the like positioned within the catheter 112 (e.g., adjacent to or downstream to the thrombectomy assembly 202) detects operation of the thrombectomy assembly 202 by way of measuring a threshold pressure or threshold flow indicative of operation of the thrombectomy assembly 202. After operation of the thrombectomy assembly 202 is detected a controller (e.g., atherectomy control 110) for the atherectomy assembly 200 is freed (capable of activation) to allow operation of the atherectomy assembly 200. Accordingly, operation of the atherectomy assembly 200 (without corresponding aspiration or infusion of fluid) is prevented in such an example until the thrombectomy assembly 202 is activated.

In another example, the operation of the thrombectomy assembly 202 during the atherectomy procedure allows for clarification of the region of the vessel 603 under investigation, for instance, through imaging. For instance, by entraining the particulate matter 1100 in the cyclical flow 600 and delivering the particulate matter along the aspiration lumen 400 the region around the plaque 610 is readily cleaned during operation of the atherectomy assembly 202. This provides the physician with an enhanced view of the plaque 610 and allows for the rapid removal of the plaque 610 without a cloud of particulate matter otherwise obscuring the remaining plaque 610 along the vessel wall 604. In another example, a contrast fluid is provided, for instance, through the thrombectomy assembly 200 to the region under investigation, for instance, adjacent to the plaque 610. Contrast fluid provided by the thrombectomy assembly allows for ready imaging and observation of the plaque 610, for instance, during or before an atherectomy procedure with the atherectomy assembly 202.

The thrombectomy assembly 200 provided in combination with the atherectomy assembly 202 leverages the capabilities of the atherectomy assembly by facilitating the removal of particulate matters such as the particulate matter 1100 from the vessel 603 during, before or after operation of the atherectomy assembly 202. Additionally, the thrombectomy assembly 200 allows for the introduction of fluids such as contrast fluids to the area under investigation to further clarify and reveal features along the vessel wall 604 such as plaque 610.

In another example, the thrombectomy assembly 200 is operated by itself before operation of the atherectomy assembly 202 to substantially clean and remove any thrombus within the region of the vessel 603 prior to operation of the atherectomy assembly 202. The clarification provided by the thrombectomy assembly 200 in the consolidated catheter 112 allows for the easy identification of the plaque 610 (having a more robust adhesion along the vessel wall 604) and thereby accelerates the atherectomy procedure by providing a clear target for the atherectomy assembly 202 including, for instance, the cutters such as the distal cutter 204, the expandable cutter 206 and the macerator 208. Optionally, the macerator 208 provides additional aspiration of particulate matter 1100, for instance, by sweeping of the particulate matter along the tapered faces 1008 of each of the projecting bars 1006. In such an example, the macerator 208 cooperates, for instance, with the thrombectomy assembly 200 to provide enhanced aspiration of particulate matter 1100 from the vessel 603.

In another example, an additional feature is included, for instance, with the catheter 112. In one example, such an additional feature includes an eccentrically mounted balloon such as the balloon 1102 shown in FIG. 11. Inflation of the balloon 1102 allows for the lateral positioning of one or more of the cutters of the atherectomy assembly 202 such as the distal cutter 204, the expandable cutter 206 and the macerator 208 relative to the vessel 603. Stated another way, the inflation of the balloon 1102 laterally biases the catheter 112, for instance, the distal catheter portion 116 relative to the plaque 610 to allow for easy removal of the plaque 610 without repeated reciprocation of the distal catheter portion 116 relative to the plaque 610. In one example, the inflatable balloon 1102 is inflated with a flow of infusion solution, for instance the balloon 1102 is coupled and in communication with the infusion tube 214 previously shown in FIG. 2.

In another example, the inflatable balloon 1102 is inflated with the back pressure from the effluent generated by the atherectomy assembly 200. Alternatively, the inflatable balloon 1102 is positioned downstream from the jet body 212 and accordingly filled by proximally directed effluent (e.g., infusion fluid and entrained particulate in the fluid). In yet another example, the balloon 1102 is inflated to bias one or more of the atherectomy assembly 200 and the thrombectomy assembly 202 toward one or more of plaque 610 and thrombus 606. Optionally, the balloon 1102 is repeatedly inflated and deflated along with rotation of the catheter 112 to reposition the balloon 1102 between each inflation. The balloon 1102 accordingly biases the rotated catheter 112 (and the thrombectomy and atherectomy assemblies 202, 200) toward thrombus or plaque according to the repositioned balloon.

VARIOUS NOTES & EXAMPLES

Example 1 can include subject matter including an atherectomy and thrombectomy system comprising: a catheter body extending from a proximal catheter portion to a distal catheter portion, the catheter body including an aspiration lumen extending from the distal catheter portion to the proximal catheter portion; an atherectomy assembly coupled with the distal catheter portion, the atherectomy assembly includes a rotatable cutter; a thrombectomy assembly coupled with the distal catheter portion, the thrombectomy assembly, the thrombectomy assembly is operable in atherectomy and thrombectomy configurations, the thrombectomy assembly includes: a jet body within the aspiration lumen, an inflow orifice extending through the catheter body and in communication with the aspiration lumen, and an outflow orifice extending through the catheter body and in communication with the aspiration lumen, the inflow orifice is closer to the jet body than the outflow orifice; in the thrombectomy configuration a cyclical flow is generated by the jet body through the outflow and inflow orifices to hydrodynamically abrade thrombus, the cyclical flow entrains thrombus and delivers thrombus into the aspiration lumen; and in the atherectomy configuration the rotatable cutter cuts plaque into plaque particulate, and the cyclical flow entrains the plaque particulate and delivers the plaque particulate into the aspiration lumen.

Example 2 can include, or can optionally be combined with the subject matter of Example 1, to optionally include wherein the atherectomy assembly includes a drive shaft coupled with the rotatable cutter and extending to the proximal catheter portion, the drive shaft is configured to rotate the rotatable cutter.

Example 3 can include, or can optionally be combined with the subject matter of one or any combination of Examples 1 or 2 to optionally include a shaft sleeve within the aspiration lumen, and the drive shaft is positioned within and rotatable relative to the shaft sleeve; and wherein the jet body in at least the atherectomy configuration generates a proximal flow of lubricating infusion fluid delivered between the shaft sleeve and the drive shaft.

Example 4 can include, or can optionally be combined with the subject matter of one or any combination of Examples 1 through 3 to optionally include wherein the atherectomy assembly includes an expandable cutter including: a spindle rotatably coupled with the distal catheter portion and coupled with the drive shaft, and one or more expandable cutting members rotatably coupled along the spindle.

Example 5 can include, or can optionally be combined with the subject matter of one or any combination of Examples 1-4 to optionally include wherein the atherectomy assembly includes a rotatable macerator including: a macerator port extending through the catheter body between an exterior port face and an interior port face, the macerator port is in communication with the aspiration lumen, a macerator core rotatably coupled with the distal catheter portion and coupled with the drive shaft, and one or more projecting bars coupled along the macerator core, the one or more projecting bars include at least one peripheral surface movably along the interior port face.

Example 6 can include, or can optionally be combined with the subject matter of Examples 1-5 to optionally include wherein the thrombectomy assembly is proximal relative to the atherectomy assembly.

Example 7 can include, or can optionally be combined with the subject matter of Examples 1-6 to optionally include wherein the jet body includes a jet loop including one or more jet orifices along the jet loop, and further comprising an infusion tube extending from the proximal catheter portion to the jet loop near the distal catheter portion.

Example 8 can include, or can optionally be combined with the subject matter of Examples 1-7 to optionally include wherein in the thrombectomy configuration the cyclical flow macerates thrombus; and in the atherectomy configuration the cyclical flow macerates the plaque particulate.

Example 9 can include, or can optionally be combined with the subject matter of Examples 1-8 to optionally include a shaft sleeve within the aspiration lumen extending from the proximal catheter portion to the distal catheter portion; and a drive shaft coupled with the rotatable cutter, the drive shaft is positioned within the shaft sleeve and the drive shaft is rotatable relative to the shaft sleeve, wherein the drive shaft is isolated from the aspiration lumen by the shaft sleeve.

Example 10 can include, or can optionally be combined with the subject matter of Examples 1-9 to optionally include an atherectomy system comprising: a catheter body extending from a proximal catheter portion to a distal catheter portion, the catheter body including an aspiration lumen extending from the distal catheter portion to the proximal catheter portion; an atherectomy assembly coupled with the distal catheter portion, the atherectomy assembly includes: a rotatable cutter, and a drive shaft coupled with the rotatable cutter and extending to the proximal catheter portion; a shaft sleeve extending through the aspiration lumen and surrounding the drive shaft, the draft shaft is rotatable relative to the shaft sleeve, and the shaft sleeve isolates the drive shaft from the aspiration lumen; a jet body positioned within the aspiration lumen near the catheter distal portion, the jet body includes at least one jet orifice directed proximally through the aspiration lumen; and an inflow orifice extending through the catheter body and in communication with the aspiration lumen, the inflow orifice is adjacent to and downstream from the jet body.

Example 11 can include, or can optionally be combined with the subject matter of Examples 1-10 to optionally include wherein in an infusion configuration the at least one jet orifice generates an infusion and lubrication stream, a lubrication portion of the infusion and lubrication stream is delivered between the shaft sleeve and the drive shaft, and an infusion portion of the infusion and lubrication stream is delivered across the inflow orifice and draws particulate matter into the aspiration lumen as a venturi.

Example 12 can include, or can optionally be combined with the subject matter of Examples 1-11 to optionally include wherein the infusion portion of the infusion and lubrication stream is delivered between the shaft sleeve and an interior surface of the catheter body.

Example 13 can include, or can optionally be combined with the subject matter of Examples 1-12 to optionally include a sheath coupled along the drive shaft, and the lubrication portion of the infusion and lubrication stream is delivered between the sheath and the drive shaft.

Example 14 can include, or can optionally be combined with the subject matter of Examples 1-13 to optionally include wherein the drive shaft includes one or more coils and a guidewire lumen within the drive shaft, and the lubrication portion of the infusion and lubrication stream is delivered between through the one or more coils to the guidewire lumen.

Example 15 can include, or can optionally be combined with the subject matter of Examples 1-14 to optionally include wherein a distal end of the shaft sleeve is distal relative to the inflow orifice and proximal relative to the jet body.

Example 16 can include, or can optionally be combined with the subject matter of Examples 1-15 to optionally include an infusion tube extending from the proximal catheter portion to the jet body near the distal catheter portion, the infusion tube is positioned between the shaft sleeve and an interior surface of the catheter body.

Example 17 can include, or can optionally be combined with the subject matter of Examples 1-16 to optionally include wherein the jet body includes a jet loop extending around the drive shaft, the jet loop is distal relative to a distal portion of the shaft sleeve.

Example 18 can include, or can optionally be combined with the subject matter of Examples 1-17 to optionally include a manifold housing, the manifold housing including: a drive motor coupled with the drive shaft, the drive motor is configured to rotate the drive shaft, an onboard battery electrically coupled with the drive motor, an infusion port coupled with an infusion tube extending through the catheter body, the jet body is coupled with the infusion tube at the distal catheter portion, and an effluent port coupled with the aspiration lumen.

Example 19 can include, or can optionally be combined with the subject matter of Examples 1-18 to optionally include wherein the rotatable cutter includes a distal tip cutter including one or more blades.

Example 20 can include, or can optionally be combined with the subject matter of Examples 1-19 to optionally include wherein the rotatable cutter includes an expandable cutter, the expandable cutter including: a spindle rotatably coupled with the distal catheter portion and coupled with the drive shaft, and one or more expandable cutting members rotatably coupled along the spindle.

Example 21 can include, or can optionally be combined with the subject matter of Examples 1-20 to optionally include a method for identifying and removing one or more of plaques or thrombus from a vessel comprising: delivering a catheter including an atherectomy system coupled with a thrombectomy system to a location within the vessel including one or more of plaque or thrombus along a vessel wall; conducting a thrombectomy procedure with the thrombectomy system including: delivering a cyclical flow of infusion fluid through outflow and inflow orifices along a catheter body at the location and hydrodynamically removing thrombus, and entraining the removed thrombus in the cyclical flow and delivering the thrombus along an aspiration lumen of the catheter body; examining the location and determining the location of a plaque along the vessel wall after thrombus is removed, the thrombectomy procedure clarifying the location for examination; and conducting an atherectomy procedure with the atherectomy system at the clarified location including: rotatably cutting the plaque with a rotatable cutter, the rotatable cutter coupled with the catheter body, and delivering the cut plaque into the aspiration lumen with the cyclical flow of infusion fluid through the outflow and inflow orifices.

Example 22 can include, or can optionally be combined with the subject matter of Examples 1-21 to optionally include wherein delivering the cut plaque into the aspiration lumen includes macerating the cut plaque with the cyclical flow.

Example 23 can include, or can optionally be combined with the subject matter of Examples 1-22 to optionally include wherein delivering the cyclical flow includes generating a proximal infusion fluid flow in the aspiration lumen, the proximal infusion fluid flow is directed across the inflow and outflow orifices, and the proximal infusion fluid flow is generated by a jet loop extending around a drive shaft coupled with the rotatable cutter.

Example 24 can include, or can optionally be combined with the subject matter of Examples 1-23 to optionally include lubricating the drive shaft with the proximal infusion fluid flow.

Example 25 can include, or can optionally be combined with the subject matter of Examples 1-24 to optionally wherein lubricating the drive shaft includes delivering the proximal infusion fluid flow at least partially between a shaft sleeve and the drive shaft rotatable relative to the shaft sleeve.

Example 26 can include, or can optionally be combined with the subject matter of Examples 1-25 to optionally include wherein rotatably cutting the plaque with a rotatable cutter includes rotatably cutting with a distal tip cutter including one or more blades.

Example 27 can include, or can optionally be combined with the subject matter of Examples 1-26 to optionally include wherein rotatably cutting the plaque with a rotatable cutter includes rotatably cutting with an expandable cutter including a spindle and one or more expandable cutting members rotatably coupled along the spindle.

Example 28 can include, or can optionally be combined with the subject matter of Examples 1-27 to optionally include wherein rotatably cutting with the expandable cutter includes laterally oscillating the expandable cutter, the expandable cutter including one or more of an unbalanced spindle or an unbalanced arrangement of expandable cutting members that oscillate the expandable cutter when rotated.

Example 29 can include, or can optionally be combined with the subject matter of Examples 1-28 to optionally include macerating the cut plaque with a macerator core having one or more projecting bars, the macerator core rotatably coupled with the catheter body, and the one or more projecting bars direct the macerated cut plaque past the jet body and the jet body delivers the macerated cut plaque along the aspiration lumen.

Example 30 can include, or can optionally be combined with the subject matter of Examples 1-29 to optionally include inflating a balloon eccentrically mounted along the catheter body, inflating the balloon biases one or more of the rotatable cutter or the inflow and outflow orifices toward a vessel wall.

Example 31 can include, or can optionally be combined with the subject matter of Examples 1-30 to optionally include wherein conducting the thrombectomy procedure is prior to conducting the atherectomy procedure.

Example 32 can include, or can optionally be combined with the subject matter of Examples 1-31 to optionally include wherein conducting the thrombectomy procedure is performed prior to and at the same time as conducting the atherectomy procedure.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An atherectomy and thrombectomy system comprising:
   a catheter body extending from a proximal catheter portion to a distal catheter portion, the catheter body including an aspiration lumen extending from the distal catheter portion to the proximal catheter portion;
   an atherectomy assembly coupled with the distal catheter portion, the atherectomy assembly includes a rotatable cutter and a drive shaft coupled with the rotatable cutter and extending to the proximal catheter portion;
   a shaft sleeve extending through the aspiration lumen and surrounding the drive shaft, the draft shaft is rotatable relative to the shaft sleeve, and the shaft sleeve isolates the drive shaft from the aspiration lumen;
   a thrombectomy assembly coupled with the distal catheter portion, the thrombectomy assembly is operable in atherectomy and thrombectomy configurations, the thrombectomy assembly includes:

a jet body positioned within the aspiration lumen near the catheter distal portion, the jet body includes at least one jet orifice directed proximally through the aspiration lumen, an inflow orifice extending through the catheter body and in communication with the aspiration lumen, the inflow orifice is adjacent to and downstream from the jet body, and an outflow orifice extending through the catheter body and in communication with the aspiration lumen, the inflow orifice is closer to the jet body than the outflow orifice;

in the thrombectomy configuration a cyclical flow is generated by the jet body through the outflow and inflow orifices to hydrodynamically abrade thrombus, the cyclical flow entrains thrombus and delivers thrombus into the aspiration lumen; and in the atherectomy configuration the rotatable cutter cuts plaque into plaque particulate, and the cyclical flow entrains the plaque particulate and delivers the plaque particulate into the aspiration lumen.

2. The atherectomy and thrombectomy system of claim 1, wherein the drive shaft is configured to rotate the rotatable cutter.

3. The atherectomy and thrombectomy system of claim 2, wherein the jet body in at least the atherectomy configuration generates a proximal flow of lubricating infusion fluid delivered between the shaft sleeve and the drive shaft.

4. The atherectomy and thrombectomy system of claim 2, wherein the atherectomy assembly includes an expandable cutter including:
a spindle rotatably coupled with the distal catheter portion and coupled with the drive shaft, and
one or more expandable cutting members rotatably coupled along the spindle.

5. The atherectomy and thrombectomy system of claim 2, wherein the atherectomy assembly includes a rotatable macerator including:
a macerator port extending through the catheter body between an exterior port face and an interior port face, the macerator port is in communication with the aspiration lumen,
a macerator core rotatably coupled with the distal catheter portion and coupled with the drive shaft, and
one or more projecting bars coupled along the macerator core, the one or more projecting bars include at least one peripheral surface movably along the interior port face.

6. The atherectomy and thrombectomy system of claim 1, wherein the thrombectomy assembly is proximal relative to the atherectomy assembly.

7. The atherectomy and thrombectomy system of claim 1, wherein
in the thrombectomy configuration the cyclical flow macerates thrombus; and
in the atherectomy configuration the cyclical flow macerates the plaque particulate.

8. An atherectomy system comprising:
a catheter body extending from a proximal catheter portion to a distal catheter portion, the catheter body including
an aspiration lumen extending from the distal catheter portion to the proximal catheter portion;
an atherectomy assembly coupled with the distal catheter portion, the atherectomy assembly includes:
a rotatable cutter, and
a drive shaft coupled with the rotatable cutter and extending to the proximal catheter portion;
a shaft sleeve extending through the aspiration lumen and surrounding the drive shaft, the draft shaft is rotatable relative to the shaft sleeve, and the shaft sleeve isolates the drive shaft from the aspiration lumen;
a jet body positioned within the aspiration lumen near the catheter distal portion, the jet body includes at least one jet orifice directed proximally through the aspiration lumen; and
an inflow orifice extending through the catheter body and in communication with the aspiration lumen, the inflow orifice is adjacent to and downstream from the jet body.

9. The atherectomy system of claim 8, wherein in an infusion configuration the at least one jet orifice generates an infusion and lubrication stream, a lubrication portion of the infusion and lubrication stream is delivered between the shaft sleeve and the drive shaft, and an infusion portion of the infusion and lubrication stream is delivered across the inflow orifice and draws particulate matter into the aspiration lumen as a venturi.

10. The atherectomy system of claim 9, wherein the infusion portion of the infusion and lubrication stream is delivered between the shaft sleeve and an interior surface of the catheter body.

11. The atherectomy system of claim 9 comprising a sheath coupled along the drive shaft, and the lubrication portion of the infusion and lubrication stream is delivered between the sheath and the drive shaft.

12. The atherectomy system of claim 9, wherein the drive shaft includes one or more coils and a guidewire lumen within the drive shaft, and the lubrication portion of the infusion and lubrication stream is delivered between through the one or more coils to the guidewire lumen.

13. The atherectomy system of claim 8, wherein a distal end of the shaft sleeve is distal relative to the inflow orifice and proximal relative to the jet body.

14. The atherectomy system of claim 8 comprising an infusion tube extending from the proximal catheter portion to the jet body near the distal catheter portion, the infusion tube is positioned between the shaft sleeve and an interior surface of the catheter body.

15. The atherectomy system of claim 14, wherein the jet body includes a jet loop extending around the drive shaft, the jet loop is distal relative to a distal portion of the shaft sleeve.

16. The atherectomy system of claim 8 comprising a manifold housing, the manifold housing including:
a drive motor coupled with the drive shaft, the drive motor is configured to rotate the drive shaft,
an infusion port coupled with an infusion tube extending through the catheter body, the jet body is coupled with the infusion tube at the distal catheter portion, and
an effluent port coupled with the aspiration lumen.

* * * * *